US011622783B2

(12) United States Patent
Strokosz et al.

(10) Patent No.: US 11,622,783 B2
(45) Date of Patent: *Apr. 11, 2023

(54) SINGLE PORT INSTRUMENTS

(71) Applicant: Applied Medical Resources Corporation, Rancho Santa Margarita, CA (US)

(72) Inventors: Arkadiusz A. Strokosz, Rancho Santa Margarita, CA (US); David T. Okihisa, Rancho Santa Margarita, CA (US); Steven E. Decker, Anaheim, CA (US); Phillip De Alday, Rancho Santa Margarita, CA (US); Scott V. Taylor, Rancho Santa Margarita, CA (US); Henry Kahle, Corona, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 545 days.

This patent is subject to a terminal disclaimer.

(21) Appl. No.: 16/579,460

(22) Filed: Sep. 23, 2019

(65) Prior Publication Data

US 2020/0029988 A1    Jan. 30, 2020

Related U.S. Application Data

(63) Continuation of application No. 14/834,137, filed on Aug. 24, 2015, now Pat. No. 10,420,576, which is a
(Continued)

(51) Int. Cl.
*A61B 17/29* (2006.01)
*A61B 17/00* (2006.01)
(Continued)

(52) U.S. Cl.
CPC .......... *A61B 17/2909* (2013.01); *A61B 90/03* (2016.02); *A61B 2017/00407* (2013.01);
(Continued)

(58) Field of Classification Search
CPC ........ A61B 17/2909; A61B 2017/2923; A61B 2017/2929; A61B 2017/2946;
(Continued)

(56) References Cited

U.S. PATENT DOCUMENTS 353,457 A    11/1886    Mills
420,741 A    2/1890    Shoots
(Continued)

FOREIGN PATENT DOCUMENTS

DE    296 23 113 U1    10/1997
EP    0 598 202    5/1994
WO    WO 2010/129035    11/2010

OTHER PUBLICATIONS

International Searching Authority, International Search Report for International Application No. PCT/US2010/052187 dated May 25, 2011.

*Primary Examiner* — Diane D Yabut
(74) *Attorney, Agent, or Firm* — John F. Heal

(57) ABSTRACT

Surgical tools that can be used in single port laparoscopic procedures can include a low-profile handle assembly to minimize tool interference adjacent the incision site. For example, a handle assembly for a surgical instrument can have a generally in-line configuration extending linearly along a central longitudinal axis of an elongate shaft of the instrument. A linkage mechanism including a trigger, an actuation link, and an actuation shaft can be positioned within the in-line handle. The linkage mechanism can be pivoted between an open position in which end effectors of the instrument are open and a toggle position in which the
(Continued)

end effectors are locked closed. A locking mechanism such as a ratchet mechanism can also be used to lock the end effectors. A surgical dissector can include gripping jaws having a curved profile or an angled elongate shaft to minimize tool interference and maximize visibility within a procedure site.

13 Claims, 14 Drawing Sheets

Related U.S. Application Data continuation of application No. 12/902,039, filed on Oct. 11, 2010, now Pat. No. 9,113,939.

(60) Provisional application No. 61/250,411, filed on Oct. 9, 2009.

(51) Int. Cl.
| | | |
|---|---|---|
| A61B 17/28 | (2006.01) | |
| A61B 17/44 | (2006.01) | |
| A61B 90/00 | (2016.01) | |

(52) U.S. Cl.
CPC ............... *A61B 2017/00424* (2013.01); *A61B 2017/00539* (2013.01); *A61B 2017/2837* (2013.01); *A61B 2017/291* (2013.01); *A61B 2017/2904* (2013.01); *A61B 2017/2922* (2013.01); *A61B 2017/2926* (2013.01); *A61B 2017/2929* (2013.01); *A61B 2017/2946* (2013.01); *A61B 2017/447* (2013.01); *A61B 2090/0811* (2016.02)

(58) Field of Classification Search
CPC ...... A61B 2017/291; A61B 2017/2837; A61B 2017/00407
See application file for complete search history.

(56) References Cited

U.S. PATENT DOCUMENTS

| | | |
|---|---|---|
| 4,433,687 A | 2/1984 | Burke et al. |
| 4,576,166 A | 3/1986 | Montgomery et al. |
| 4,598,711 A | 7/1986 | Deniega |
| 5,147,380 A | 9/1992 | Hernandez et al. |
| 5,184,625 A | 2/1993 | Cottone, Jr. et al. |
| 5,201,743 A | 4/1993 | Haber et al. |
| 5,250,073 A | 10/1993 | Cottone, Jr. |
| 5,251,638 A | 10/1993 | Cottone, Jr. et al. |
| 5,275,613 A | 1/1994 | Haber et al. |
| 5,275,614 A | 1/1994 | Haber et al. |
| 5,281,235 A | 1/1994 | Haber et al. |
| 5,282,806 A | 2/1994 | Haber et al. |
| 5,290,302 A | 3/1994 | Pericic |
| 5,314,424 A | 5/1994 | Nicholas |
| 5,330,502 A | 7/1994 | Hassler et al. |
| 5,348,259 A | 9/1994 | Blanco et al. |
| 5,354,313 A | 10/1994 | Boebel |
| 5,366,476 A | 11/1994 | Noda |
| 5,368,600 A | 11/1994 | Failla et al. |
| 5,368,605 A | 11/1994 | Miller, Jr. |
| 5,374,277 A | 12/1994 | Hassler |
| 5,382,254 A | 1/1995 | McGarry et al. |
| 5,383,888 A | 1/1995 | Zvenyatsky et al. |
| 5,397,046 A | 3/1995 | Savage et al. |
| 5,403,342 A | 4/1995 | Tovey et al. |
| 5,409,478 A | 4/1995 | Gerry et al. |
| 5,413,583 A | 5/1995 | Wohlers |
| 5,417,203 A | 5/1995 | Tovey et al. |
| 5,425,705 A | 6/1995 | Evard et al. |
| 5,431,675 A | 7/1995 | Nicholas et al. |
| 5,468,250 A | 11/1995 | Paraschac et al. |
| 5,470,328 A | 11/1995 | Furnish et al. |
| 5,472,132 A | 12/1995 | Savage et al. |
| 5,489,290 A | 2/1996 | Furnish |
| 5,490,819 A | 2/1996 | Nicholas et al. |
| 5,498,256 A | 3/1996 | Furnish |
| 5,501,698 A | 3/1996 | Roth et al. |
| 5,514,157 A | 5/1996 | Nicholas et al. |
| 5,522,830 A | 6/1996 | Aranyi |
| 5,522,839 A | 6/1996 | Pilling |
| 5,536,251 A | 7/1996 | Evard et al. |
| 5,603,723 A | 2/1997 | Aranyi et al. |
| 5,618,306 A | 4/1997 | Roth et al. |
| 5,618,307 A | 4/1997 | Donlon et al. |
| 5,620,415 A | 4/1997 | Lucey et al. |
| 5,624,431 A | 4/1997 | Gerry et al. |
| 5,626,607 A | 5/1997 | Malecki et al. |
| 5,626,608 A | 5/1997 | Cuny et al. |
| 5,643,294 A | 7/1997 | Tovey et al. |
| 5,649,957 A | 7/1997 | Levin |
| 5,665,105 A | 9/1997 | Furnish et al. |
| 5,669,875 A | 9/1997 | van Eerdenburg |
| 5,683,412 A | 11/1997 | Scarfone |
| 5,700,275 A | 12/1997 | Bell et al. |
| 5,827,279 A | 1/1998 | Hughett et al. |
| 5,730,740 A | 3/1998 | Wales et al. |
| 5,735,873 A | 4/1998 | MacLean |
| 5,766,205 A | 6/1998 | Zvenyatsky et al. |
| 5,782,834 A | 7/1998 | Lucey et al. |
| 5,782,859 A | 7/1998 | Nicholas et al. |
| 5,785,647 A | 7/1998 | Tompkins et al. |
| 5,792,165 A | 8/1998 | Klieman et al. |
| 5,792,178 A | 8/1998 | Welch et al. |
| 5,797,956 A | 8/1998 | Furnish et al. |
| 5,800,449 A | 9/1998 | Wales |
| 5,810,877 A | 9/1998 | Roth et al. |
| 5,817,119 A | 10/1998 | Klieman et al. |
| 5,827,263 A | 10/1998 | Furnish et al. |
| 5,827,323 A | 10/1998 | Klieman et al. |
| 5,836,960 A | 11/1998 | Kolesa et al. |
| 5,855,590 A | 1/1999 | Malecki et al. |
| 5,861,024 A | 1/1999 | Rashidi |
| 5,893,835 A | 4/1999 | Witt et al. |
| 5,893,873 A | 4/1999 | Rader et al. |
| 5,904,702 A | 5/1999 | Ek et al. |
| 5,921,996 A | 7/1999 | Sherman |
| 5,922,007 A | 7/1999 | Hoogeboom et al. |
| 5,928,263 A | 7/1999 | Hoogeboom |
| 5,954,746 A | 9/1999 | Holthaus et al. |
| 6,007,561 A | 12/1999 | Bourque et al. |
| 6,117,158 A | 9/2000 | Measamer et al. |
| 6,322,578 B1 | 11/2001 | Houle et al. |
| 6,368,340 B2 | 4/2002 | Malecki et al. |
| 6,436,122 B1 | 8/2002 | Frank et al. |
| 6,440,144 B1 | 8/2002 | Bacher |
| 6,443,968 B1 | 9/2002 | Holthaus et al. |
| 6,554,829 B2 | 4/2003 | Schulze et al. |
| 6,533,797 B1 | 8/2003 | Stone et al. |
| 6,635,071 B2 | 10/2003 | Boche et al. |
| 6,641,595 B1 | 11/2003 | Moran et al. |
| 6,666,854 B1 | 12/2003 | Lange |
| 6,676,676 B2 | 1/2004 | Danitz et al. |
| 6,685,715 B2 | 2/2004 | Danitz et al. |
| 6,719,776 B2 | 4/2004 | Baxter et al. |
| 6,755,338 B2 | 6/2004 | Hahnen et al. |
| 6,818,005 B2 | 11/2004 | Kupferschmid et al. |
| 6,958,070 B2 | 10/2005 | Witt et al. |
| 6,976,969 B2 | 12/2005 | Messerly |
| 7,083,620 B2 | 8/2006 | Jahns et al. |
| 7,087,071 B2 | 8/2006 | Nicholas et al. |
| 7,094,202 B2 | 8/2006 | Nobis et al. |
| 7,108,703 B2 | 9/2006 | Danitz et al. |
| 7,476,237 B2 | 1/2009 | Taniguchi et al. |
| 7,481,348 B2 | 1/2009 | Marczyk |
| 8,512,315 B2 | 8/2013 | Leonard et al. |
| 2003/0074014 A1 | 4/2003 | Castaneda |
| 2004/0073254 A1 | 4/2004 | Wyman et al. |
| 2004/0260335 A1 | 12/2004 | Braun |
| 2005/0143774 A1 | 6/2005 | Polo |
| 2005/0187575 A1 | 8/2005 | Hallbeck et al. |

(56) References Cited

U.S. PATENT DOCUMENTS

| | | |
|---|---|---|
| 2006/0020287 A1 | 1/2006 | Lee |
| 2006/0020288 A1 | 1/2006 | Leonard |
| 2006/0079933 A1 | 4/2006 | Hushka |
| 2007/0225754 A1 | 9/2007 | Measamer |
| 2007/0276430 A1 | 11/2007 | Lee et al. |
| 2007/0282371 A1 | 12/2007 | Lee et al. |
| 2008/0015631 A1 | 1/2008 | Lee et al. |
| 2008/0154299 A1 | 1/2008 | Livneh |
| 2008/0065116 A1 | 3/2008 | Lee et al. |
| 2008/0262537 A1 | 10/2008 | Lee et al. |
| 2008/0294191 A1 | 11/2008 | Lee |
| 2009/0048625 A1 | 1/2009 | Pedersen et al. |
| 2009/0054732 A1 | 2/2009 | Markham |
| 2009/0088792 A1 | 4/2009 | Hoell et al. |
| 2009/0131974 A1 | 5/2009 | Pedersen et al. |
| 2009/0171147 A1 | 7/2009 | Lee |
| 2009/0192521 A1 | 7/2009 | Braun |
| 2009/0198272 A1 | 8/2009 | Kerver et al. |

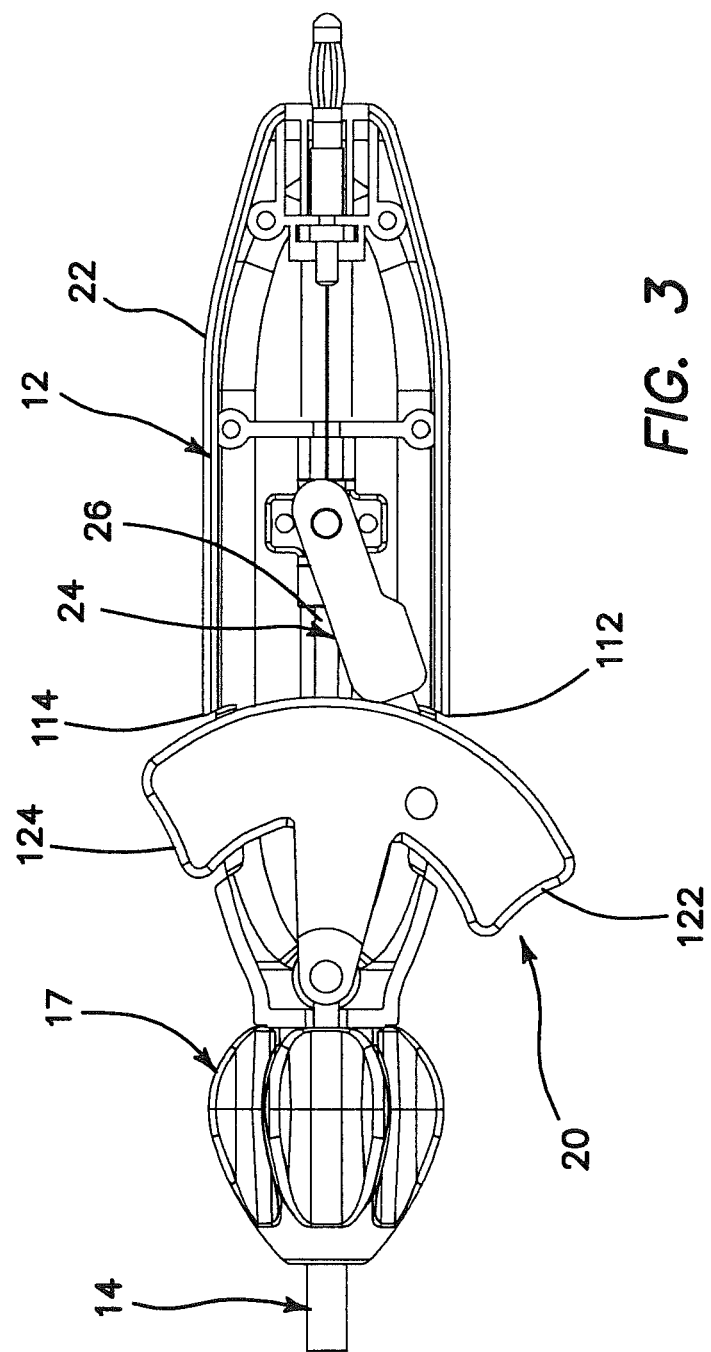

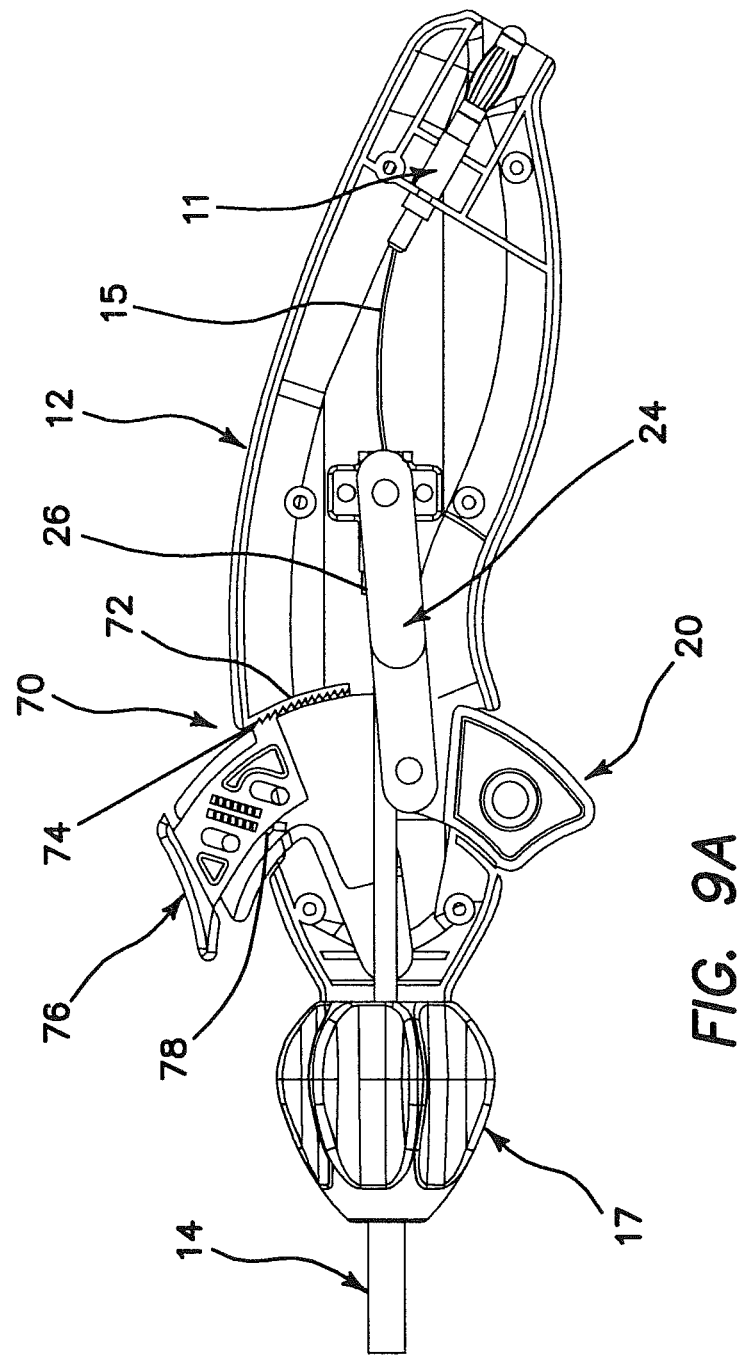

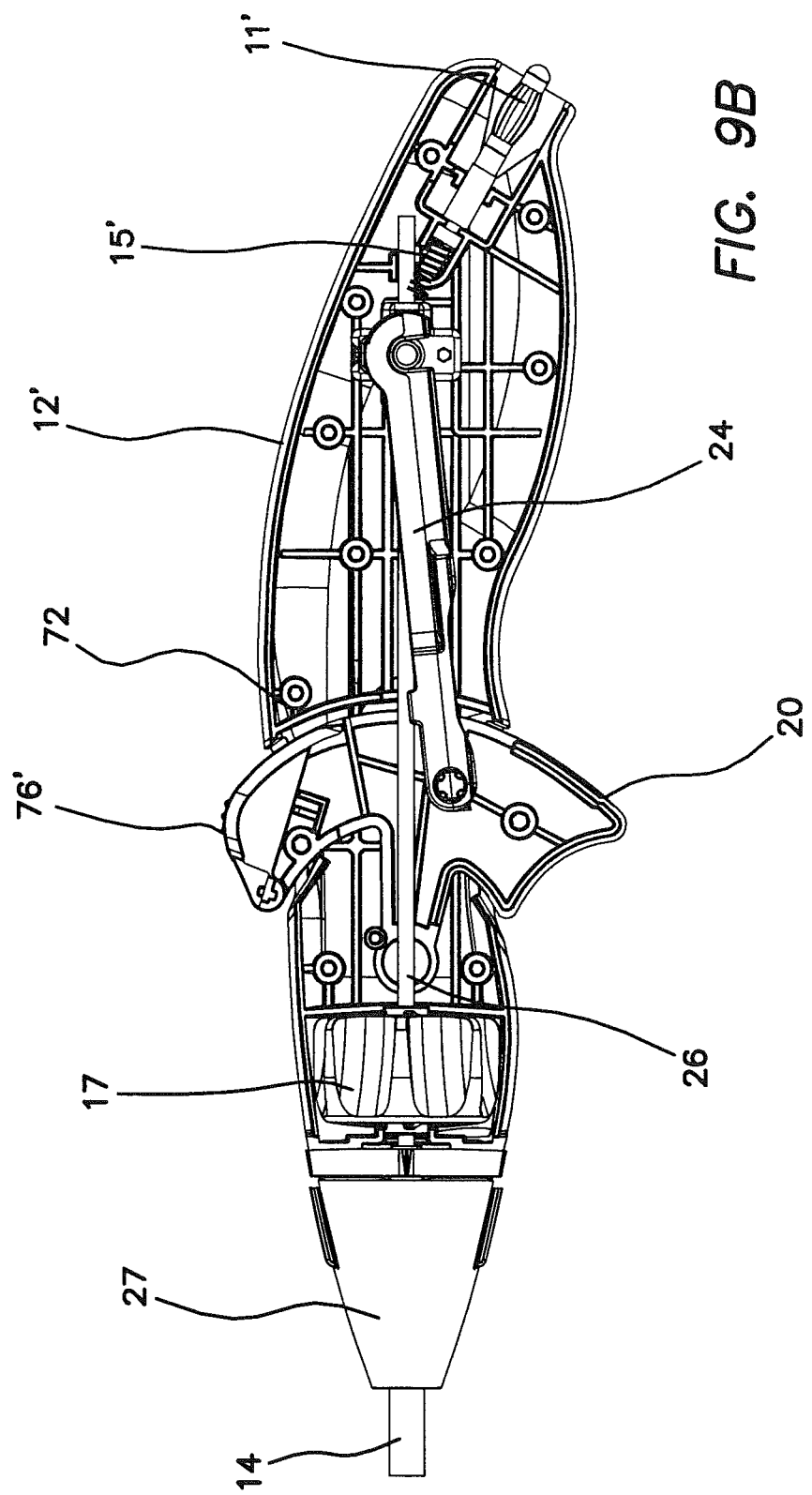

SINGLE PORT INSTRUMENTS

CROSS REFERENCE TO RELATED APPLICATIONS

This application is a continuation of U.S. patent application Ser. No. 14/834,137, entitled "SINGLE PORT INSTRUMENTS," filed Aug. 24, 2015, which issued as U.S. Pat. No. 10,420,576, which is a continuation of U.S. patent application Ser. No. 12/902,039, entitled "SINGLE PORT INSTRUMENTS," filed Oct. 11, 2010, which issued as U.S. Pat. No. 9,113,939, which claims the benefit of U.S. Provisional Patent Application No. 61/250,411, entitled "SINGLE PORT INSTRUMENTS," filed Oct. 9, 2009. The above-referenced applications are each incorporated by reference herein in their entireties.

BACKGROUND OF THE INVENTION

Field of the Invention

The present application relates to devices for use in general or laparoscopic surgery, and, more particularly, to surgical devices useful in single port surgeries.

Description of the Related Art

Various single port surgical procedures can be performed using a single incision in the body of the patient and passing all instruments used during the surgery through that incision. While a single, relatively small incision site has various advantages for the patient, the single access port can often lead to difficulty in handling of the instruments. With a single incision site, the handles of various surgical instruments compete for the limited space outside of the incision, and the elongated instrument shafts are positioned almost parallel to each other in a limited space inside the incision. This substantially parallel instrument shaft configuration often leads to limited visibility of the surgical site as the laparoscope is positioned along the other instrument shafts, limiting the angle in which the tips of the instruments are visible. The novel devices described herein are designed to ease the restrictions posed by single port surgeries and make it easier for the operating surgeon to perform the surgery.

SUMMARY OF THE INVENTION

In some embodiments, a surgical instrument is provided comprising a handle assembly, an elongate shaft, and an end effector assembly. The handle assembly has a proximal end and a distal end. The elongate shaft extends from the distal end of the handle assembly along a central longitudinal axis. The elongate shaft has a distal end opposite the handle assembly. The end effector assembly is disposed at the distal end of the elongate shaft. The handle assembly has an in-line configuration extending generally linearly from the proximal end to the distal end thereof. The handle assembly further comprises a handle body and a linkage mechanism. The linkage mechanism comprises a trigger, an actuation link, and an actuation shaft. The trigger is pivotably coupled to the handle body. The trigger is pivotable between an open position in which the end effector assembly is in an open state, and a toggle position in which the end effector assembly is locked in a closed state. The actuation link is pivotably coupled to the trigger and extends generally proximally within the handle body. The actuation shaft is pivotably coupled to the actuation link and longitudinally slidable with respect to the elongate shaft responsive to pivotal movement of the trigger.

In certain embodiments, a surgical instrument is provided comprising a handle assembly, an elongate shaft, an end effector assembly, a first rotation mechanism, and a second rotation mechanism. The handle assembly has a proximal end and a distal end. The elongate shaft extends from the distal end of the handle assembly. The elongate shaft has a proximal end and a distal end. The elongate shaft comprises a proximal segment, an angled segment, and a distal segment. The proximal segment extends from the proximal end of the elongate shaft along a central longitudinal axis. The angled segment is between the proximal end and the distal end of the elongate shaft. The angled segment has a bend angle. The distal segment extends transversely to the central longitudinal axis by the bend angle from the angled segment to the distal end of the elongate shaft. The end effector assembly is disposed at the distal end of the elongate shaft. The first rotation mechanism has a first actuator rotatably coupling the end effector to the elongate shaft. The second rotation mechanism has a second actuator rotatably coupling the elongate shaft to the handle assembly. The handle assembly has an in-line configuration extending generally linearly from the proximal end to the distal end thereof.

In certain embodiments, a surgical instrument is provided comprising a handle assembly, an elongate shaft, and an end effector assembly. The elongate shaft extends distally from the handle assembly and defines a central longitudinal axis. The end effector assembly comprises a pair of jaws. The pair of jaws is operably coupled to the elongate shaft. Each of the jaws has a proximal end coupled to the elongate shaft and a distal end opposite the proximal end. Each of the jaws comprises a curved profile between the proximal end and the distal end defined by an angular arc length of at least 35 degrees and an offset distance from the central longitudinal axis of at least 0.3 inches.

BRIEF DESCRIPTION OF THE DRAWINGS

FIG. 3 is a cut away top view of the low profile handle assembly of FIG. 1 with a linkage mechanism in an open position;

FIG. 9A is a partial cut away view of an embodiment of handle assembly having a ratchet mechanism for a surgical instrument;

FIG. 9B is a partial cut away view of another embodiment of handle assembly for a surgical instrument;

DETAILED DESCRIPTION OF THE INVENTION

Figure 1:
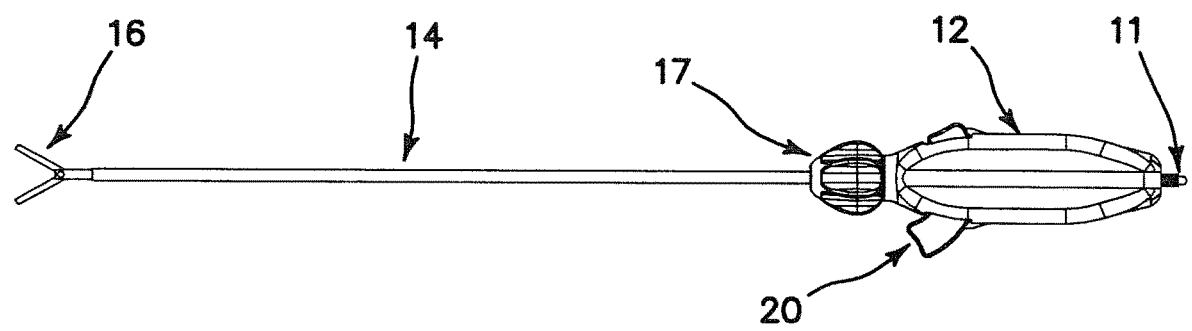
FIG. 1 is a side view of an embodiment of surgical instrument having a low-profile handle assembly.

With reference to FIG. 1, an embodiment of surgical instrument 10 that can be used in single port surgical procedures is illustrated. The surgical instrument 10 comprises a handle assembly 12, an elongate shaft 14 extending from a distal end of the handle assembly 12, and an end effector assembly 16 coupled to a distal end of the elongate shaft. In various embodiments of surgical instrument, the end effector assembly 16 can comprise grasping jaws, dissecting jaws, or cutting scissors or another surgical tool. In some embodiments, the surgical instrument 10 can include an electrical connector 11 electrically coupled to the end effector assembly 16, wherein the end effector assembly 16 includes an electrosurgical tool.

In some embodiments, the elongate shaft 14 and end effector assembly 16 can be sized to pas through an access port such as a trocar cannula having a predetermined size. For example, the surgical instruments 10 described herein can be sized for use in conjunction with a 5 mm trocar cannula, a 10 mm trocar cannula, a 12 mm trocar cannula, a 15 mm trocar cannula, or another trocar cannula size.

In some embodiments, the handle assembly 12 has a low-profile configuration extending generally longitudinally with respect to a longitudinal axis defined by the elongate shaft 14 of the surgical instrument 10 in an in-line configuration. In some embodiments, the handle assembly 12 can extend generally longitudinally with a curved ergonomic grip portion (FIGS. 9A-9D) to facilitate user gripability and further enhance user comfort. Advantageously, the low-profile handle minimizes the size of the instrument extending proximally from the incision site, thus reducing the incidence of interference with other surgical tools adjacent the incision site.

Figure 2A:
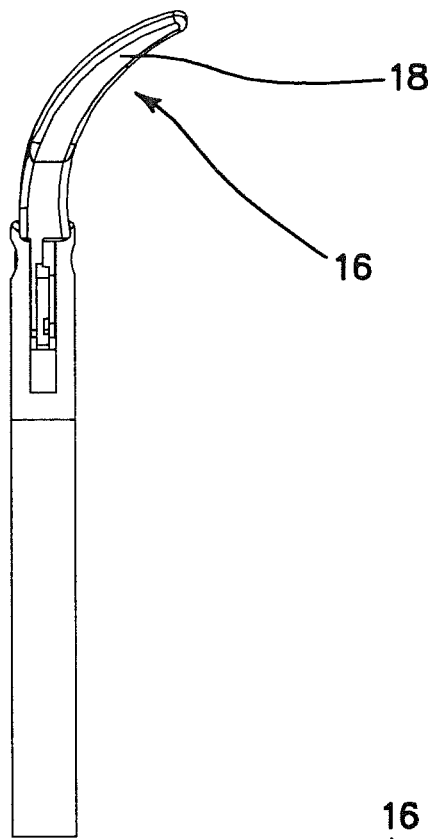
FIG. 2A is a top view of a jaw assembly of an embodiment of surgical dissector having a curved jaw configuration.
Figure 2B:
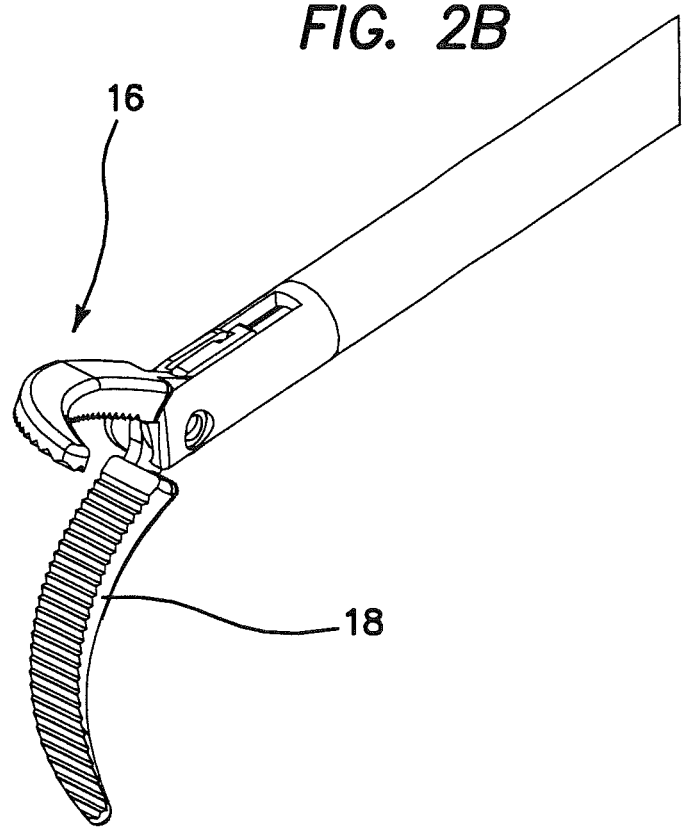
FIG. 2B is a perspective view of the jaw assembly of FIG. 2A.

With reference to FIGS. 2A and 2B, one embodiment of end effector assembly 16 with dissector jaws 18 having a curved profile is illustrated. Advantageously, the curved profile of the dissector jaws 18 allows the end effector assembly to grasp tissue offset from other surgical instruments inserted through a single insertion site. The jaws with the curved profile can move the distal end of the device off the centerline of the elongate shaft and improve the visualization of the distal end. The curve of the distal end also improves access to the tissue structures that are positioned behind other body formations.

In some embodiments, the curved profile can define an angular arc of about 60 degrees. Desirably, the curved profile can define an angular arc of greater than about 35 degrees. In other embodiments, the curved profile can define an angular arc of between about 35 degrees and about 110 degrees, desirably, the curved profile can define an angular arc of between about 45 degrees and about 95 degrees, and more desirably, the curved profile can define an angular arc of between about 55 degrees and about 65 degrees.

Figure 4:
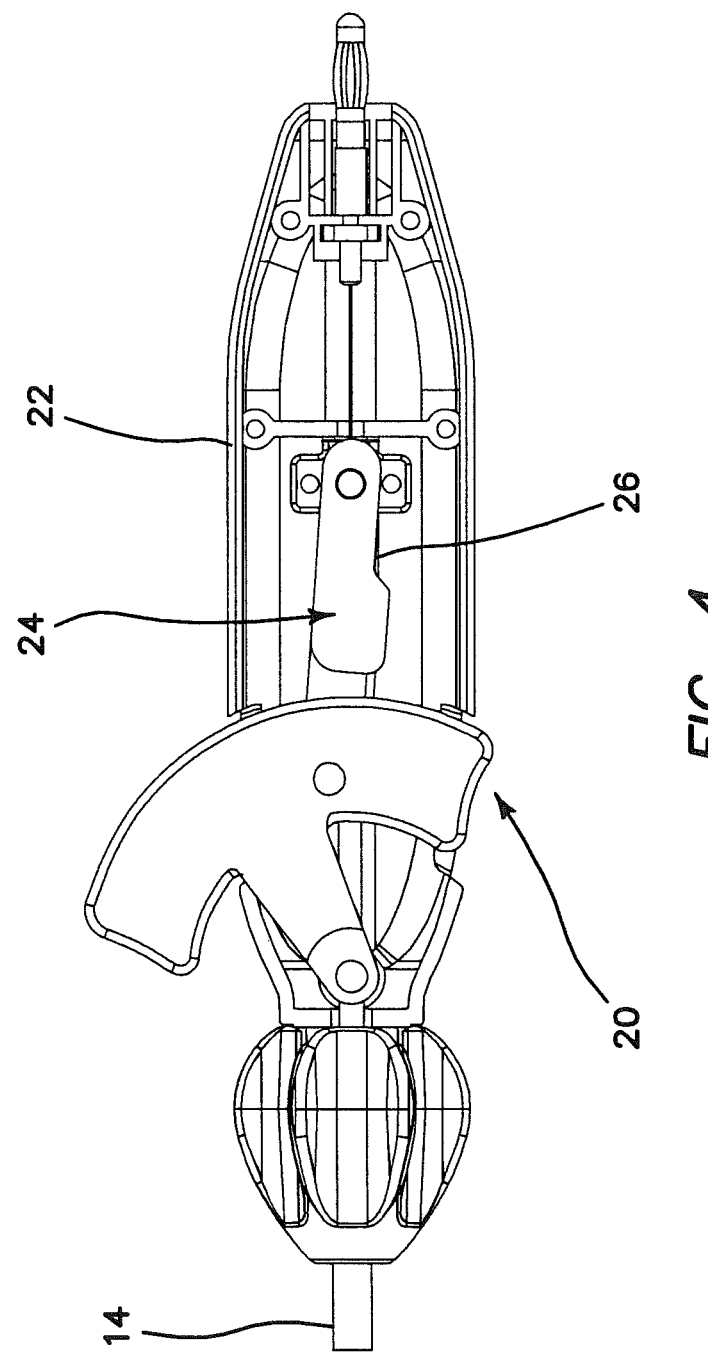
FIG. 4 is a cut away top view of the low profile handle assembly of FIG. 1 with the linkage mechanism in a toggle position.

With reference to FIGS. 3 and 4, the opening and closing of the end effector assembly 16 of the device 10 can be accomplished by alternately pushing a shuttle-like trigger 20 from one side of the handle assembly 12 to the other. In some embodiments, a handle body 22 of the handle assembly 12 can include a first aperture 112 and a second aperture 114 generally diametrically opposed to the first aperture 112. The trigger 20 can comprise a first actuation surface 122 and a second actuation surface 124 opposite the first actuation surface. A pivot such as a pivot pin can couple the trigger 20 to the handle body 22 at a point between the first actuation surface 122 and the second actuation surface 124. With the trigger in a first, or open position, the first actuation surface 122 can extend out of and protrude from the first aperture 112, as illustrated in FIG. 3. With the trigger in a second, or toggle position, the second actuation surface 124 can extend out of and protrude from the second aperture 114, as illustrated in FIG. 4.

With continued reference to FIGS. 3 and 4, in some embodiments, the instrument 10 can comprise a rotation mechanism rotatably coupling the end effector assembly 16 to the handle assembly 12. In some embodiments, the handle assembly 12 can include a rotatable knob 17 that is coupled to the elongate shaft 14 and can be used to rotate the elongate shaft 14 and the end effector assembly 16 about the central longitudinal axis of the elongate shaft 14. In the illustrated embodiment, the rotatable knob 17 is disposed at the distal end of the handle assembly 12. In some embodiments, the rotatable knob 17 and the elongate shaft 14 are rotatable 360 degrees with respect to the handle assembly 12. In other embodiments, the handle assembly 12 can include stops to define the rotatable motion of the rotatable knob 17 and the elongate shaft to an angular range less than 360 degrees. In some embodiments, as described further herein, the handle assembly can include an additional rotation mechanism to rotate the end effector assembly 16 up to 360 degrees independently with respect to the elongate shaft 14 as well.

In some embodiments, the handle of the laparoscopic surgical instrument 10 can be symmetrical, which would allow for the rotation of the end effector assembly 16 to be accomplished by the rotation of the handle assembly 12 itself. In other embodiments, the handle assembly 12 can have a non-symmetrical ergonomic shape. With non-symmetrical handles, the surgical instrument can desirably include a rotatable knob as described above such that rotation of the end effector assembly can be accomplished by rotating the rotatable knob in the handle assembly. The in-line, symmetrical, handle configuration allows for placement and movement of two or more handles close to each other, without creating undue handle interference due to their sizes. The handle can be rotated 360 degrees in the palm of the user allowing for the comparable rotation of the distal end effector assembly 16, without using the rotating knob 17. The rotating knob 17 can also be used for the same purpose, if necessary. In some embodiments, the shuttle trigger 20 design protrudes only slightly outside of the low profile handle assembly 12, without taking much space and it is connected by the linkage mechanism to the actuating rod.

With continued reference to FIGS. 3 and 4, the handle assembly 12 can include a linkage mechanism to actuate the end effector assembly. The linkage mechanism can be coupled to the handle body 22 of the handle assembly 12. As illustrated, the linkage mechanism comprises a trigger 20, pivotably coupled to the handle body 22, an actuation link 24 pivotably coupled to the trigger 20 at a first end of the actuation link 24, and an actuation shaft 26 pivotably coupled to the actuation link 24 at a second end of the actuation link 24. In the illustrated embodiment, the trigger 20 is pivotably coupled to the handle body 22 near a distal end of the handle body, the actuation link 24 is pivotably coupled to the trigger proximal of the coupling between the trigger 20 and handle body 22, and the actuation link 24 is pivotably coupled to the actuation shaft 26 proximal of the coupling between the trigger 20 and the actuation link 24. In other embodiments, the trigger, actuation link, and actuation shaft could have different geometries and arrangements to operatively couple to the end effector assembly.

The actuation shaft 26 can be either a rigid member such as a metal or a plastic rod or tube, or a flexible member such as a wire or a cable. Movement of the trigger 20 to actuate the linkage mechanism between the open position and the toggle position longitudinally slides the actuation shaft 26 with respect to the elongate shaft 14. The actuation shaft 26 can extend at least partially within the elongate shaft 14 and can be operatively coupled to the end effector assembly 16.

FIG. 3 illustrates the linkage mechanism in an open position such that the end effector assembly 16 is open (e.g., jaws of a grasper or blades of scissors are spaced apart from one another). FIG. 4 illustrates the linkage mechanism in a toggle position such that the end effector assembly 16 is closed (e.g., jaws of a grasper or blades of scissors are contacting one another). With the linkage mechanism in the toggle position, movement of the trigger 20 pivots the actuation link 24 into a toggle position to lock the end effector assembly 16 in the closed position. Thus, advantageously, the linkage mechanism described herein can include a locking mechanism that can be used to prevent the end effector assembly 16 from opening inadvertently.

An advantage of the illustrated linkage mechanism design is that the same shuttle trigger 20 can be used to close/open as well as to lock/unlock the end effector assembly 16 of the device. The lock is activated by actuating the shuttle trigger 20, closing the end effector assembly 16 on the tissue, and exerting the additional pressure on the trigger 20 to push the connected linkage over the centerline of the device, moving the linkage mechanism into the toggle position. The linkage or shaft deformation can be utilized to limit end effector assembly pressure exerted during the toggle creation. The end effector assembly 16 can be opened again by pushing the shuttle trigger in the opposite direction. As discussed in greater detail with reference to FIG. 9, in some embodiments, an additional or separate locking mechanism can be positioned in the handle assembly.

Advantageously, with a surgical instrument having a low-profile handle and linkage mechanism as illustrated in FIGS. 1, 3, and 4, a medical practitioner is provided with relatively free and unrestricted movement of the handles proximal to the surgical incision and good tip visibility at the surgical site distal to the surgical incision. These advantages are particularly evident in surgical procedures with limited space within the operation site such as procedures that utilize a single access port.

Figure 5:
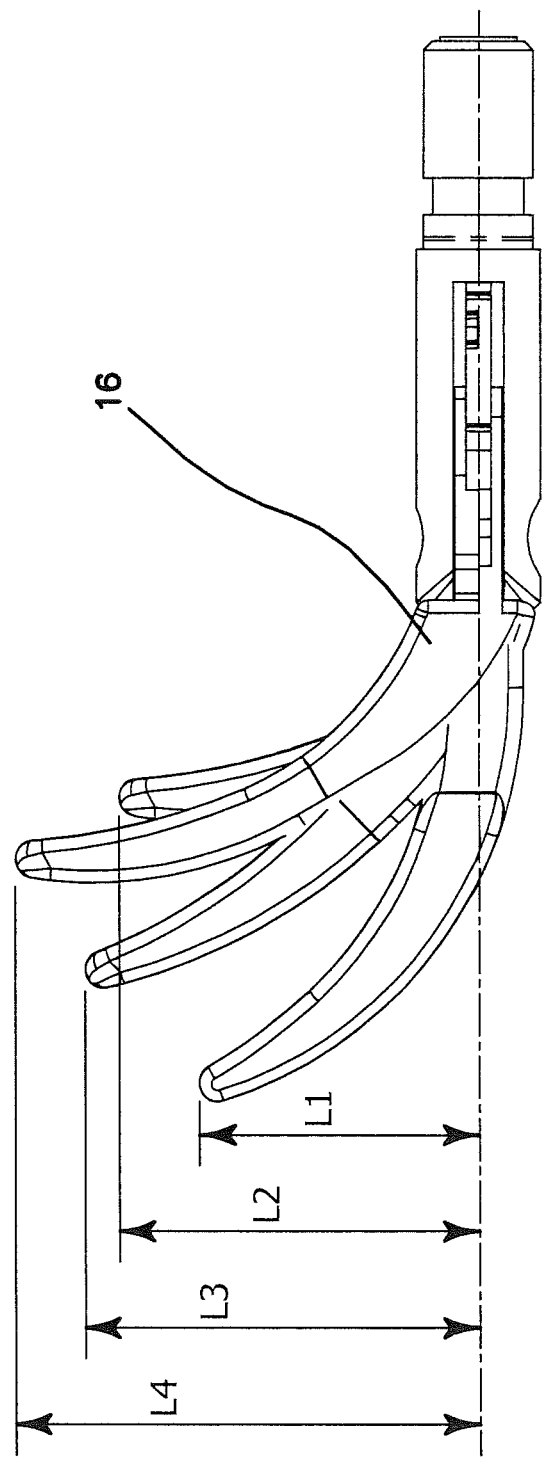
FIG. 5 is a top view of various embodiments of jaw assembly for a surgical instrument having various curved jaw profiles.

With reference to FIG. 5, in some embodiments of surgical device having end effector assemblies 16 with jaws, the jaws can be manufactured with different size curves and/or with different lengths. For example, as discussed above with reference to FIG. 2, the angle of curvature of the jaws with reference to the elongate shaft can include an arcuate profile between about 35 degrees and about 110 degrees, desirably, the curved profile can define an angular arc of between about 45 degrees and about 95 degrees, and more desirably, the curved profile can define an angular arc of between about 55 degrees and about 65 degrees. Moreover, in the illustrated embodiments, an offset distance, L1, L2, L3, L4 between a tip of the jaws and a central longitudinal axis, A of the elongate shaft of the surgical instrument can range between approximately 0.457 inches and approximately 0.763 inches. In certain embodiments, the offset distance can be at least approximately 0.3 inches. In some embodiments, the offset distance can be between approximately 0.3 inches and 1.0 inches, desirably, the offset distance can be between approximately 0.45 inches and 0.85 inches, and more desirably, the offset distance can be between 0.55 inches and 0.70 inches. Tip visualization and access to the tissue structures can be optimized by varying the curved profile and offset distance of jaws of an end effector assembly.

Figure 6:
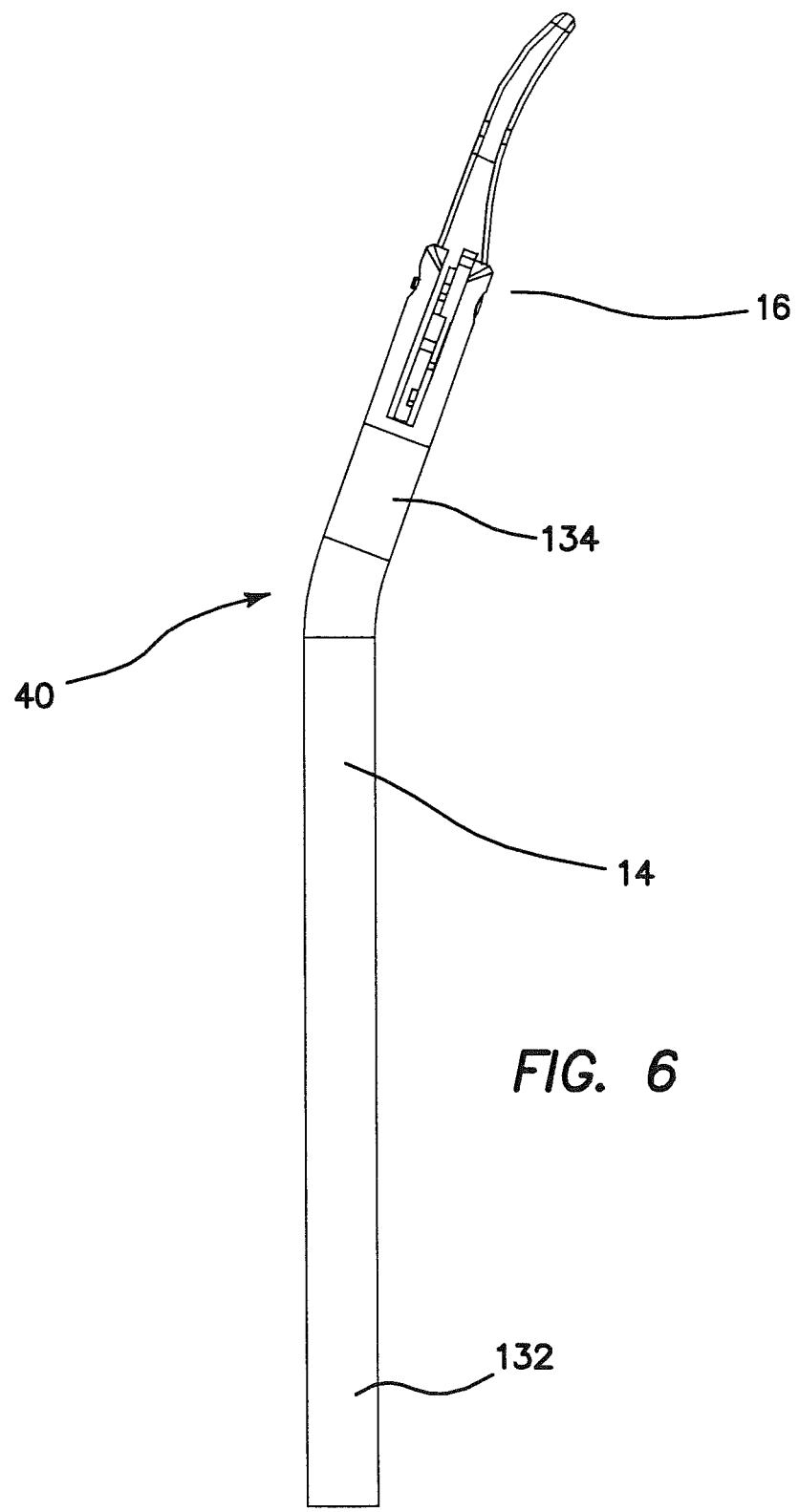
FIG. 6 is a top view of an angled shaft and jaw assembly for a surgical instrument having an independently rotatable jaw assembly.

With reference to FIG. 6, in some embodiments, the elongate shaft 14' can comprise an angled segment 40 that would allow for better tip visualization and improved access to the tissue structures that are positioned behind other body formations. Thus, the elongate shaft 14' can comprise a proximal segment 132 extending from a proximal end of the elongate shaft along a central longitudinal axis, an angled segment 40 between the proximal end and the distal end of the elongate shaft, and a distal segment 134 extending transversely to the central longitudinal axis from the angled segment to the distal end of the elongate shaft. The angled segment 40 has a bend angle defining the transverse relationship of the distal segment 134 to the central longitudinal axis. In some embodiments, the bend angle can be greater than about 20 degrees. In some embodiments, the bend angle can be between about 20 degrees and about 45 degrees.

With continued reference to FIG. 6, advantageously, a surgical instrument having an angled elongate shaft 14' can be used in a single port procedure in conjunction with another surgical instrument having a straight elongate shaft 14 such that a surgeon can position the end effector assemblies of the instruments in close proximity to one another while the handle assemblies of the instruments are spaced apart from one another to facilitate manipulation of the surgical instruments.

Figure 7:
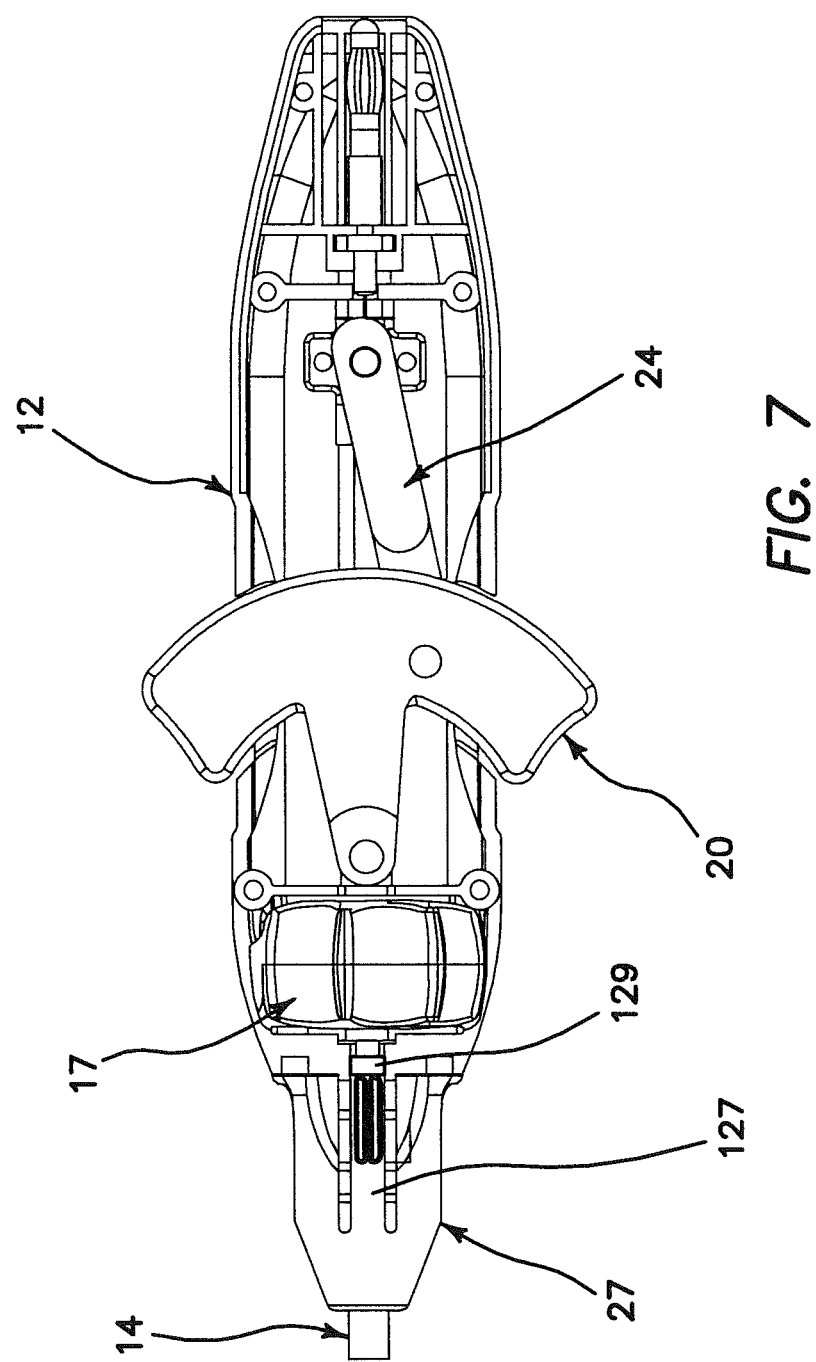
FIG. 7 is a partial cut away view of a handle assembly for the surgical instrument of FIG. 6.

With reference to FIG. 7, an embodiment of handle assembly 12 that can be used with the angled elongate shaft 14' of FIG. 6 is illustrated. The handle assembly 12 can include a first rotation mechanism rotatably coupling the end effector assembly 16 to the elongate shaft 14' and a second rotation mechanism rotatably coupling the elongate shaft 14' to the handle assembly 12. In the illustrated embodiment, the handle assembly 12 includes a first rotation mechanism having a rotatable actuator such as a rotatable knob 17 positioned between the proximal end and the distal end of the handle assembly 12 and rotatably coupled to the handle assembly. As illustrated, rotatable knob 17 rotates a clevis/jaw assembly within the angled shaft 14' to rotate the end effector assembly 16 relative to the shaft 14'. In some embodiments, the end effector assembly can be rotated 360 degrees relative to the elongate shaft 14' using rotatable knob 17. In other embodiments, rotation of the end effector assembly relative to the elongate shaft 14' can be restricted to a predetermined angular range.

With continued reference to FIG. 7, as illustrated, the handle assembly 12 also includes a second rotation mechanism having a rotatable knob 27 positioned at the distal end of the handle assembly 12 and rotatably coupled to the handle assembly 12. The rotatable knob 27 rotates the angled elongate shaft 14' relative to the handle assembly 12. In some embodiments, the elongate shaft 14' can be rotated and fixed at predetermined stops in predetermined angular increments, such as, for example 180 degree angle increments. Thus, the second rotation mechanism can be rotated to a first position at a first predetermined stop that positions the angled elongate shaft 14' such that the surgical instrument can be used in a surgeon's right hand while another instrument is in the surgeon's left hand. The second rotation mechanism can be selectively rotated to a second position at a second predetermined stop rotationally 180 degrees angularly spaced from the first predetermined stop that positions the angled elongate shaft 14' such that the surgical instrument can be used in a surgeon's left hand while another instrument is in the surgeon's right hand. In other embodiments, the predetermined stops can be arranged as desired in different angular spacings. For example, in some embodiments, a second rotation mechanism can have four predetermined stops, angularly spaced 90 degrees apart from one other to define an orientation of the elongate shaft 14' for right handed operation, an orientation of the elongate shaft 14' for left handed orientation, an orientation of the elongate shaft 14' allowing positioning above another surgical instrument, and an orientation of the elongate shaft 14' allowing positioning below another surgical instrument.

With continued reference to FIG. 7, in some embodiments, the predetermined stops of the second rotation mechanism are defined by selectively engageable features formed on the rotatable knob 27 and the handle assembly 12. The rotatable knob 27 can comprise a latch member 127 coupled thereto which is engageable with one or more recesses, such as detents 129 formed at the distal end of the handle assembly to define a predetermined stop.

With continued reference to FIG. 7, in some embodiments, the handle assembly 12 can include an electrical connector 11' that is recessed into the body of the handle. As illustrated, an electrical connection pin does not extend distally beyond a distal end of the handle assembly, and the electrical connection pin is positioned within a recess in the body of the handle. Advantageously, such a recessed electrical connector 11' can enhance user safety when working with electrosurgical devices. Also, advantageously, the recessed electrical connector 11' can enhance the low profile configuration of the handle assembly, reducing the risk of collisions between the electrical connector and hands or fingers of medical practitioners or collisions with other surgical instruments at the surgical site.

Figure 8:
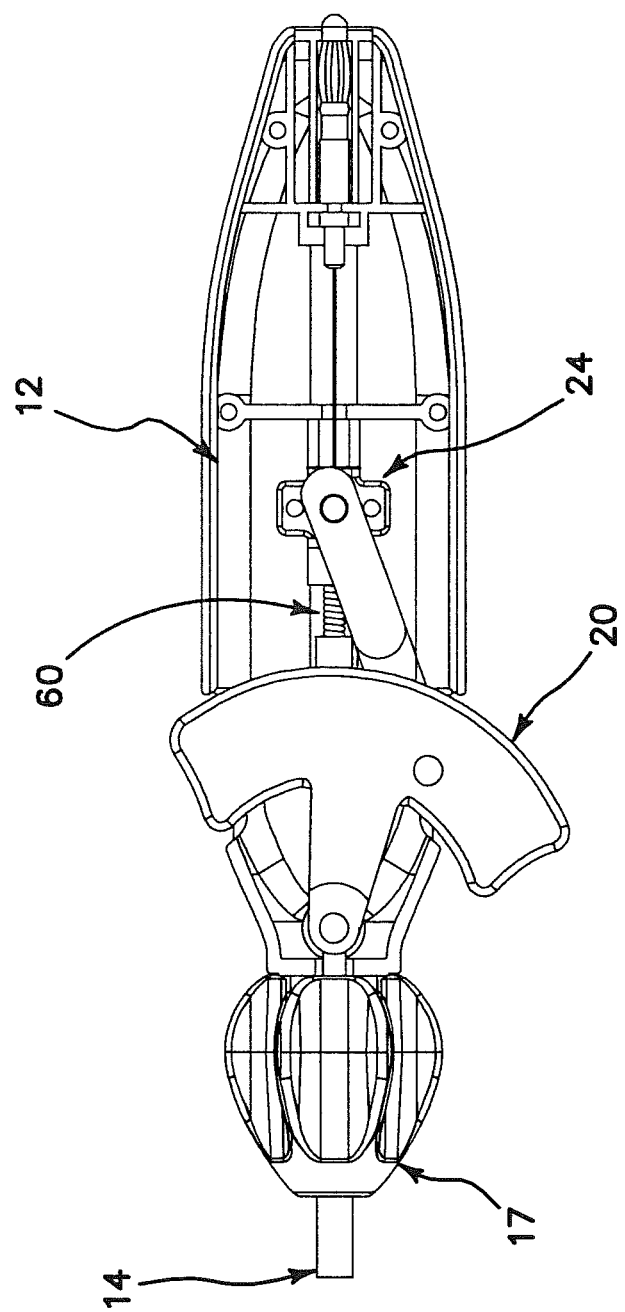
FIG. 8 is a partial cut away view of an embodiment of handle assembly having a constant force spring for a surgical instrument.

With reference to FIG. 8, an embodiment of handle assembly for surgical instrument is illustrated. The end effector assembly of the surgical instrument can be locked in place upon placing trigger 20 and the linkage mechanism in the toggle position as described above with reference to FIGS. 3 and 4. In the embodiment of FIG. 8, the linkage mechanism includes a spring 60 that can be placed between the actuation shaft 26 and the actuation linkage 24, facilitating the toggle position creation. The spring 60 would compress (or extend) when the tension or compression forces reach a predetermined value, associated with the spring rate, limiting the jaw's clamping force and establishing the force required to place the linkage in the toggle position. For example, once the shaft pulling force reaches predetermined amount (i.e. 70 lbs), the spring starts compressing (or extending), limiting amount of force applied to the jaws. Any additional linkage and trigger movement stretches (or compresses) the spring only, without applying more force to the actuating rod. Thus, advantageously, a predetermined constant force can be applied to tissue retained by the end effector assembly 16 using the illustrated linkage mechanism. Once the linkage is pushed over the actuating rod's centerline, the linkage is in the toggle position, preventing the jaws from opening. Pressing on the shuttle trigger 20 in the opposite direction, stretches (or compresses) the spring 60 again, which allows the linkage to be pushed back over the rod's centerline, releasing the end effector assembly 16.

Figure 9C:
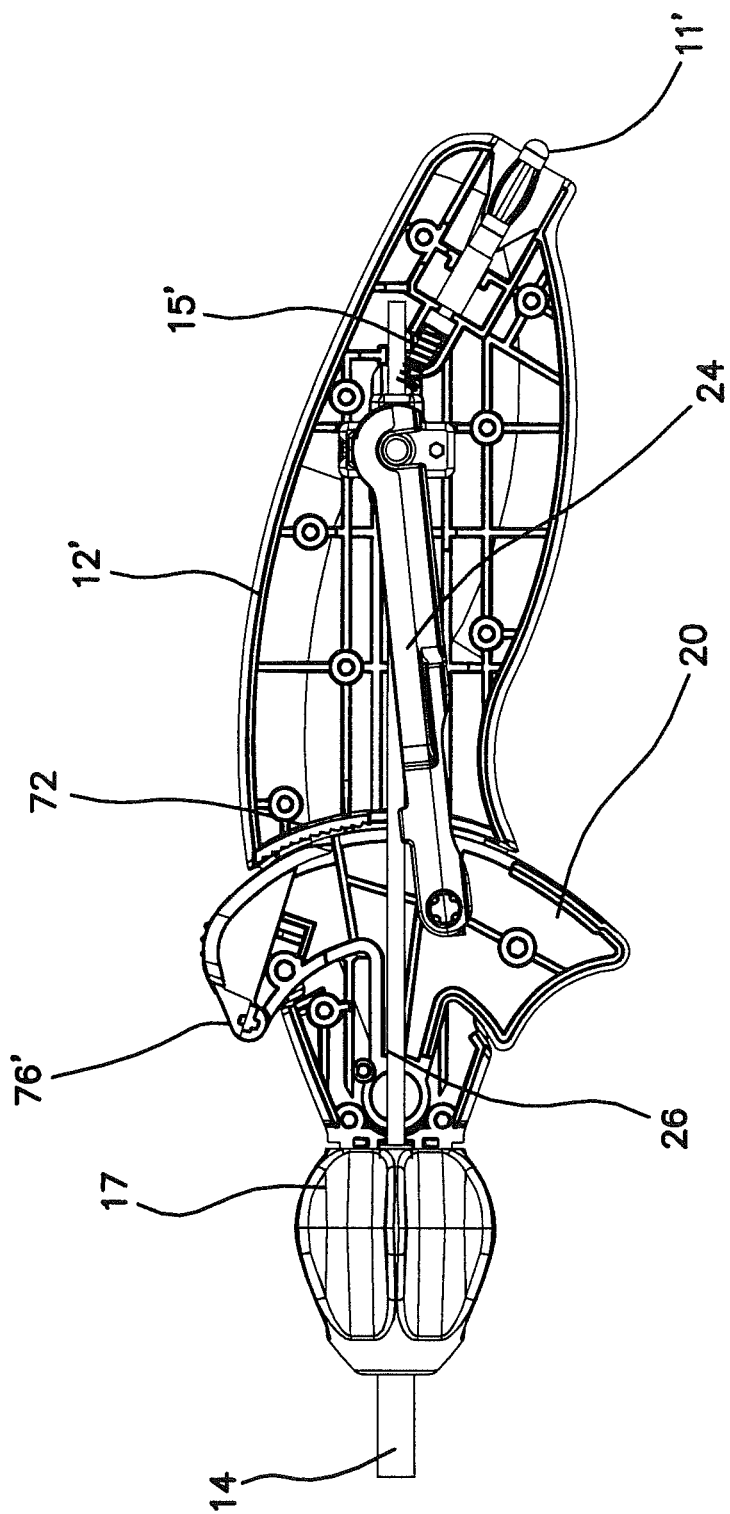
FIG. 9C is a partial cut away view of another embodiment of handle assembly for a surgical instrument.
Figure 9D:
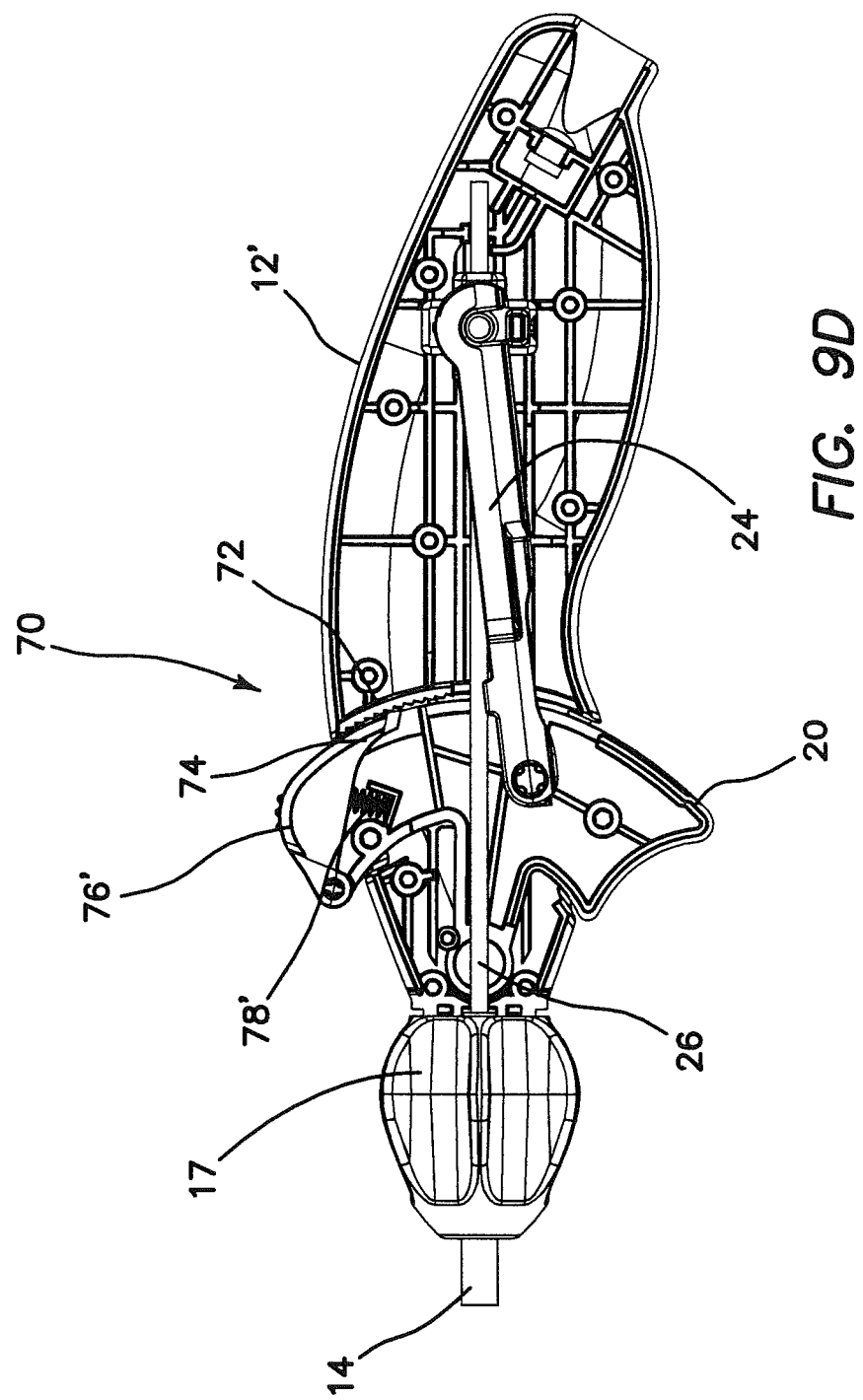
FIG. 9D is a partial cut away view of another embodiment of handle assembly having a ratchet mechanism for a surgical instrument.

With reference to FIGS. 9A and 9D, in some embodiments of handle assembly 12', instead of or in addition to using the toggle mechanism described above to lock the end effector assembly 16 in a closed position, a shuttle trigger ratchet mechanism 70 on the linkage mechanism can be used to lock the end effector assembly 16. The ratchet mechanism 70 comprises a ratchet 72 having at least one latched position that can prevent the shuttle trigger 20 from moving towards an open position with respect to the handle assembly 12, preventing movement of the linked actuation shaft 26 and locking the jaws or other end effector. The ratchet mechanism 70 is movable to a free position in which the trigger 20 can be moved freely towards the open or closed position. The ratchet 72 of the ratchet mechanism can comprise one or more teeth positioned on the handle body. A corresponding spring loaded pawl 74 can be positioned on the shuttle trigger 20. The pawl 74 can be configured to engage the teeth of the ratchet 72, defining the one or more latched positions. As illustrated, the ratchet 72 has multiple teeth, allowing incremental latched positions between a fully open and a fully closed end effector assembly.

With continued reference to FIGS. 9A and 9D, the pawl 74 can be operatively coupled to a release button 76, 76' positioned on the trigger 20. By pressing the release button 76, 76', the pawl 74 is moved away from the ratchet 72 teeth, allowing for free movement of the trigger 20. For example, with the ratchet mechanism 70 in a latched position, the release button 76, 76' can be pressed to allow movement of the trigger 20 to the open position. Moreover, in some instances, it can be desirable to allow free movement of the trigger from the open position to the closed position without the spring loaded pawl engaging the ratchet. Thus, the release button 76, 76' can be pressed during actuation of the trigger towards a closed position. If desired, the pressure on the release button can be removed to engage the ratchet during such a closing actuation.

With continued reference to FIGS. 9A and 9D, desirably, the release button 76, 76' can be positioned on an actuation surface of the trigger 20. In the illustrated embodiment, the release button 76 is positioned on a second or upper actuation surface of the shuttle trigger 20. As illustrated, a user will naturally press the upper actuation surface to move the trigger 20 towards an open configuration. Thus, advantageously, this placement of the release button 76, 76' facilitates release of the ratchet mechanism to a free position when it is desired to open the end effector assembly. The release button 76, 76' can be biased such that the pawl 74 is biased towards engagement with the ratchet 72 teeth. For example, a biasing member such as a coil spring 78, 78' can bear on the trigger 20 and the release button 76, 76' to urge the pawl 74 into engagement with the ratchet 72 teeth.

Various assemblies can be used to couple the release button 76, 76' to the trigger 20 at the upper actuation surface to allow this disengagement. For example, in the embodiments of handle assembly 12' illustrated in FIG. 9A, the release button 76 is slidably coupled to the trigger 20. The illustrated slidable coupling includes posts or pins coupled to the trigger 20 sliding in slots formed in the release button 76, although in other embodiments, other sliding assemblies are contemplated. In the embodiment of handle assembly 12' illustrated in FIG. 9D, the release button 76 is pivotably coupled to the trigger 20 about a pivot point at a distal corner of the upper actuation surface of the trigger 20.

With reference to FIGS. 9A-9D, in certain embodiments of surgical instrument, the handle assembly 12', while extending generally longitudinally, can include a curved grip portion to enhance the ergonomic experience to a user without substantially diminishing the ability of multiple surgical instruments to be positioned within a single surgical port. Thus, advantageously, in some embodiments, the handle assembly 12' can be slightly asymmetric, providing improved comfort to the user, without any substantial size increase. Moreover, various features discussed herein with respect to certain embodiments of the surgical instruments can be combined in various embodiments of handle assembly. For example, FIG. 9B illustrates a handle assembly 12' with no ratchet mechanism and FIG. 9C illustrates a handle assembly 12' with no ratchet mechanism for use with an angled elongate shaft having two rotation mechanisms and two corresponding rotatable knobs 17, 27, similar to those discussed above with respect to FIG. 7 as certain surgical instruments, for example, scissors and dissectors can be effective without the use of a ratchet, while other instruments, for example, graspers can advantageously include a ratchet mechanism. In the embodiments of FIGS. 9B and 9C, the handle assembly 12' includes ratchet teeth to provide manufacturing efficiencies and commonality of parts with other surgical instruments including ratchet mechanisms. In other embodiments of surgical instruments without a ratchet mechanism, the handle assembly can be free of ratchet teeth. FIG. 9D illustrates a handle assembly 12' having an ergonomic curved grip portion, a ratchet mechanism 70, and no electrical connector. It is contemplated that various other combinations of the features discussed herein can be made in various other embodiments of surgical instruments within the scope of the present application.

With reference to FIGS. 9A and 9B in certain embodiments, electrical coupling of the electrical connector 11' to the actuation shaft 26 can comprise an electrically conductive member such as an electrically conductive wire 15 or an electrically conductive spring 15'. In some embodiments, the electrically conductive member electrically contacts the electrical connector 11' and the actuation rod 26 and is sized to maintain electrical contact with the electrical connector 11' and the actuation rod 26 throughout an actuation cycle of the actuation rod 26 from an open position of the end effector assembly to a closed position of the end effector assembly.

Figure 10:
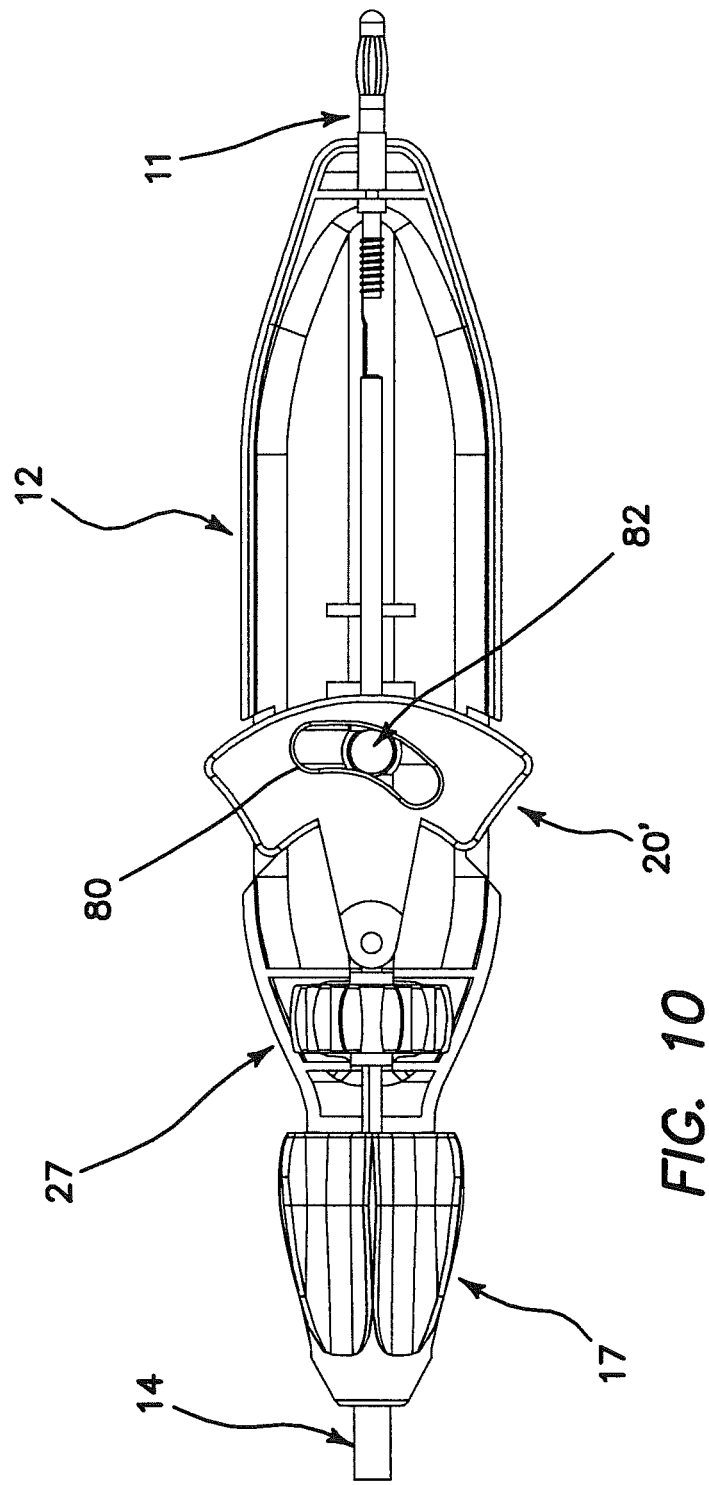
FIG. 10 is a partial cut away view of a handle assembly having a pin slot linkage mechanism for a surgical instrument.

With reference to FIG. 10, another embodiment of handle assembly having a linkage mechanism is illustrated. In the illustrated embodiment, the opening and closing of the end effector assembly of the instrument can be accomplished by means of a slotted trigger 20' and a pin 80 connected to the actuation shaft 26 of the device. The pin 80 travels inside and is constrained by the slot 82 in the trigger 20. By pressing the shuttle trigger 20 in either direction, the pin 80 and the connected actuation shaft 26 follows the profile of the slot in the trigger 20, opening and closing the end effector assembly of the instrument.

Figure 11:
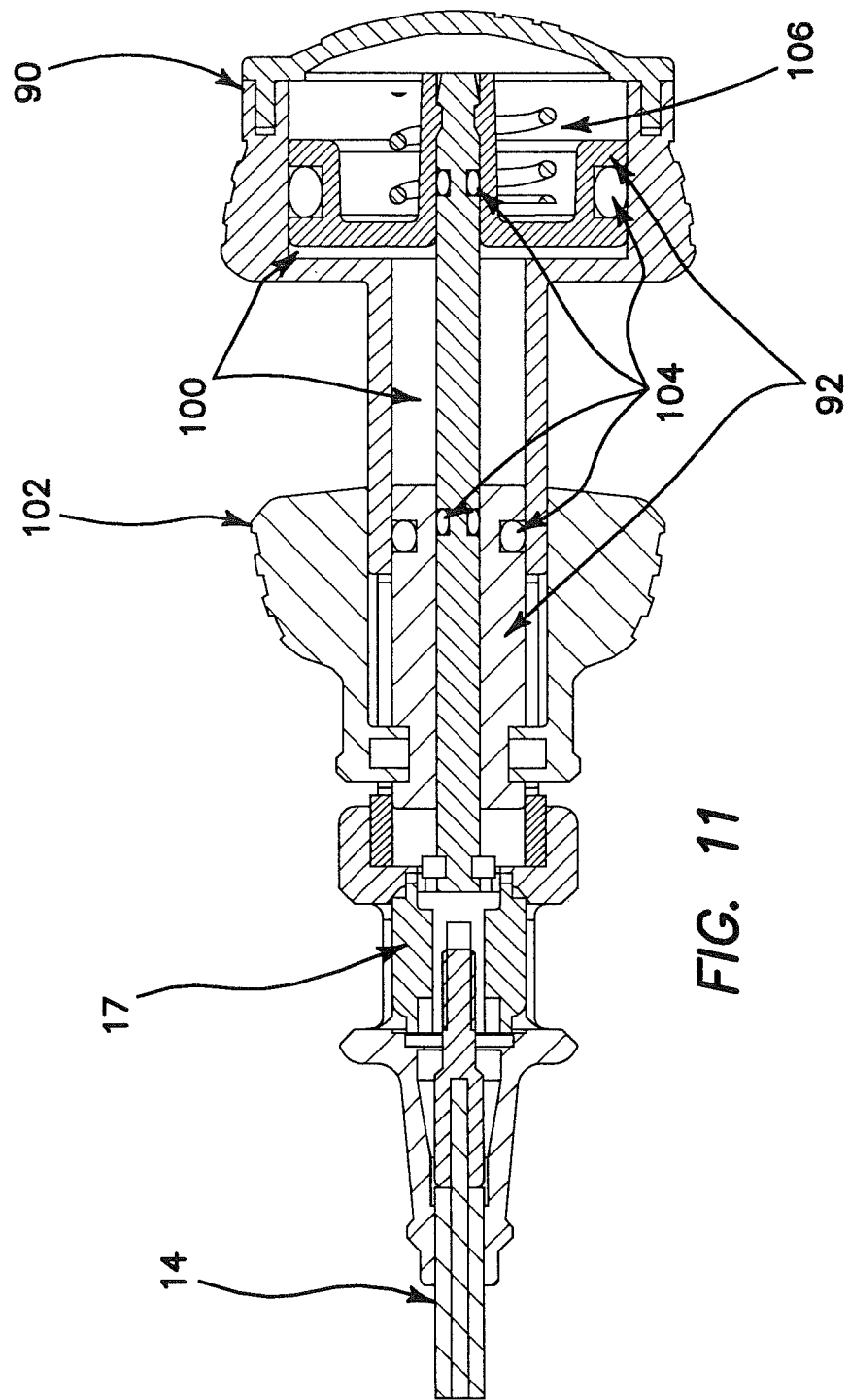
FIG. 11 is a partial cut away view of a handle assembly having a hydraulic actuation mechanism for a surgical instrument.

With reference to FIG. 11, in some embodiments, the opening and closing of the end effector assembly 16 of a surgical instrument can be accomplished by means of hydraulic action provided by an incompressible fluid 100 such as saline, mineral oil, or a gel. The fluid can be stored inside the handle 90 and moved by pulling a small diameter piston 92 coupled with a movable handle 102. The pressure created by the fluid movement would push a large diameter piston connected to the actuation shaft, which is connected to the jaws of the instrument, causing the jaws to close. The hydraulic circuit can be sealed at appropriate locations with gaskets or other seals 104 such as O-rings. The incompressible fluid can be used to generate a high tensile force on the actuation shaft with a minimal user input force. The force multiplier in the handle is equal to the ratio of the areas of the pistons. The hydraulic action enables the handle to deliver the appropriate jaw actuation force and to be designed in a small compact configuration to fit in the palm of a surgeon's hand. The handle could also be designed to push the actuation rod to close the instrument jaws. The handle could also include a compression spring 106 to return the instrument jaws to an open configuration.

In some embodiments, a smoke evacuation channel/path can be added to the instrument design. A connector can be added to the handle to which a vacuum line can be attached. The connector can be placed onto a handle or on top of the shaft. The smoke generated during electrosurgery can then be drawn inside the instrument shaft and out through the connector in the shaft or in the handle. The instruments could alternatively include a vent cap with a manual valve to enable smoke generated during electrosurgery to be vented though the shaft.

During clinical use, an access device such as a trocar or Gelpoint™ is first placed through a body wall creating an opening across the body wall. The instrument is then inserted through the seal of the access device until the distal end of the instrument extends beyond the body wall opening and positioned adjacent to the operating site. The grasper/dissector jaws or scissors are then used to manipulate or cut tissue by pressing on the shuttle trigger.

In some embodiments, a method of manufacture of the novel instruments is injection molding of the plastic components and machining or casting of the metal components.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A surgical instrument comprising:
   a handle assembly having a proximal end and a distal end;
   an elongate shaft extending from the distal end of the handle assembly along a central longitudinal axis, the elongate shaft having a distal end opposite the handle assembly; and
   an end effector assembly disposed at the distal end of the elongate shaft;
   wherein the handle assembly further comprises:
      a handle body comprising an exterior surface, a first aperture formed in the exterior surface and a second aperture formed in the exterior surface and diametrically opposed to the first aperture; and
      a linkage mechanism comprising:
         a trigger pivotably coupled to the handle body near the distal end of the handle assembly, the trigger comprising a first end extendable from the first aperture and a second end extendable from the second aperture, the trigger being pivotable between an open position in which the first end extends from the first aperture and the end effector assembly is in an open state, and a closed position in which the second end extends from the second aperture and the end effector assembly is in a closed state;

an actuation link pivotably coupled to the trigger between the first end and the second end and extending generally proximally within the handle body;

an actuation shaft pivotably coupled to the actuation link proximal of the coupling of the actuation link with the trigger, the actuation shaft being longitudinally slidable with respect to the elongate shaft responsive to pivotal movement of the trigger; and a ratchet mechanism to selectively latch the trigger to the handle body.

2. The surgical instrument of claim 1, wherein the ratchet mechanism comprises a plurality of teeth positioned in the handle body.

3. The surgical instrument of claim 2, wherein the plurality of teeth is positioned adjacent the second aperture in the handle body.

4. The surgical instrument of claim 2, wherein the ratchet mechanism comprises a pawl positioned on the trigger.

5. The surgical instrument of claim 4, wherein the ratchet mechanism further comprises a release button coupled to the pawl.

6. The surgical instrument of claim 5, wherein the release button is positioned at the second end of the trigger.

7. The surgical instrument of claim 6, wherein the release button is positioned to unlatch the ratchet mechanism when the trigger is moved from the closed position towards open position.

8. The surgical instrument of claim 1, wherein the ratchet mechanism has at least one latched position.

9. The surgical instrument of claim 8, wherein the ratchet mechanism has a plurality of incremental latched positions between the open state and the closed state of the end effector assembly.

10. A surgical instrument comprising:

a handle assembly having a proximal end and a distal end;

an elongate shaft extending from the distal end of the handle assembly along a central longitudinal axis, the elongate shaft having a distal end opposite the handle assembly; and an end effector assembly disposed at the distal end of the elongate shaft;

wherein the handle assembly extends generally linearly from the proximal end to the distal end thereof; and wherein the handle assembly further comprises:

a handle body having an outer surface and comprising a first aperture in the outer surface and a second aperture in the outer surface opposite the first aperture; and a linkage mechanism comprising:

a shuttle pivotably coupled to the handle body near the distal end of the handle assembly and extending across the handle body between the first aperture and the second aperture, the shuttle comprising a first surface extendable from the first aperture of the handle body and a second surface extendable from the second aperture and pivotable between a first position in which the first surface protrudes from the first aperture and a second position in which the second surface protrudes from the second aperture, wherein movement of the shuttle between the first position and the second position actuates the end effector assembly; and a ratchet mechanism to selectively lock the shuttle to the handle body.

11. The surgical instrument of claim 10, wherein the second surface of the shuttle comprises a release button for the ratchet mechanism to selectively unlock the shuttle from the handle body.

12. The surgical instrument of claim 10, further comprising an electrical connector recessed into the handle body.

13. The surgical instrument of claim 12, wherein the linkage mechanism comprises an actuation shaft operably coupled to the shuttle and the end effector and further comprising one of an electrically conductive spring and an electrically conductive wire electrically coupling the electrical connector to the actuation shaft.

* * * * *